United States Patent
Beller et al.

(10) Patent No.: US 6,825,377 B1
(45) Date of Patent: Nov. 30, 2004

(54) METHOD FOR THE DIHYDROXYLATION OF OLEFINS USING TRANSITION METAL CATALYSTS

(75) Inventors: Matthias Beller, Rostock (DE); Christian Döbler, Lichtenhagen-Dorf (DE); Gerald Mehltretter, Rostock (DE); Uta Sundermeier, Rostock (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/019,996
(22) PCT Filed: Apr. 18, 2000
(86) PCT No.: PCT/EP00/03493
§ 371 (c)(1),
(2), (4) Date: Oct. 19, 2001
(87) PCT Pub. No.: WO00/64848
PCT Pub. Date: Nov. 2, 2000

(30) Foreign Application Priority Data

Apr. 25, 1999 (DE) .......................................... 199 20 038

(51) Int. Cl.[7] .............................................. C07C 69/66
(52) U.S. Cl. ........................ 560/186; 560/129; 560/179
(58) Field of Search ................................ 560/186, 179, 560/128, 189

(56) References Cited

U.S. PATENT DOCUMENTS

| 2,769,824 A | | 11/1956 | Schneider et al. ..... 260/397.45 |
| 3,317,592 A | * | 5/1967 | MacLean et al. |
| 4,496,779 A | | 1/1985 | Myers et al. ................ 568/860 |

FOREIGN PATENT DOCUMENTS

| EP | 0077201 | 4/1983 |
| GB | 1028940 | 5/1966 |
| WO | 93/17150 | 9/1993 |

OTHER PUBLICATIONS

Asymmetric Dehydroxylation Reactions (month unavailable) 1996, pp. 1009–1024, Diols via Catalytic Dihydroxylation, Matthias Beller, K. Barry Sharpless.
Chem. Rev. (month unavailable) 1994, 94, pp. 2483–2547, Catalytic Asymmertric Dihydroxylation, Hartmuth C. Kolb, Michael S. VanNieuwenhze, and K. Barry Sharpless.
Synthesis, (month unavailable) 1984, pp. 85–127, α–Amidoalkylation at Carbon: Recent Advances—Part I, Harold E. Zaugg.
Tetrahedron Letters No. 48, pp 4907–4908, (month unavailable) 1972, An Improved Procedure for the KmnO₄ Oxidation of Olefins to C1S–1,2,Glycols by use of Phase Transfer Catalysis, William P. Weber and James Peter Shepherd.

J. Org. Chem. (month unavailable) 1997, 62, 2453–2457, A Concise and Convenient Synthesis of DL–proto–Quercitol and DL–gala–Quercitol via Ene Reaction of Singlet Oxygen Combined with [2+4] Cycloaddition to Cyclohexadiene, Emine Salamci, Hasan Secen, Yasar Sütbeya, and Metin Balci.
Liebigs Ann/Recueil (month unavailable) 1997, pp. 1029–1034, New Synthesis of 28–Homobrassinolide from Stigmasterol, Braja G. Hazra, Tirunahari Pavan Kumar, and Padmakar L. Joshi.
J. Chem. Research (S). (month unavailable) 1996 pp. 400–401, Ruthenium Tetraoxide Oxidation of Alkenes. Part 7. A more Complete Picture, Laura Albarella, Vincenzo Picciali, Dian Smaldone and Donato Sica.
Chem. Eur. J. (month unavailable) 1996, 2, No. 1, pp. 50–57, Ruthenium–Catalyzed cis–Dihydroxylation of Alkenes: Scope and Limitations, Tony K. M. Shing, Eric K. W. Tam, Vincent W.–F. Tai, Ivan H. F. Chung, and Qin Jiang.
Bull Chem. Soc. Jpn., 70, pp. 2535–2540 (month unavailable) (1997) A Chemo–Enzymatic Synthesis of D–Allosamine Derivatives from Tri–O–acetyl– D–glucal, Takeshi Sugai, Hanako Okazaki, Atsuhito Kuboki, and Hiromichi Ohta.
Synlett (month unavailable) 1995, pp. 1014–1016, Synthesis and cis–Dihydroxylation of 6H–1,2–Oxazines Synthesis of Dihydroxyprolinols, Jörg Angermann, Kai Homann, Hans–Ulrich Reissig, Reinhold Zimmer.
Carbohydrate Research 304 (month unavailable) (1997) pp. 39–42, A practical multigram–scale synthesis of allo–inositol, Michel Desjardins, Larry E. Brammer Jr., Thomas Hudlicky.
Tetrahedron 54 (month unavailable) (1998) pp. 6605–6626, Syntheses of Novel Hydroxylamine Carbanucleosides, Mark J. Mulvihill and Marvin J. Miller.
Chem. Ber (month unavailable) (1908), 45, O. Makowka: Zur Kenntnis des Osmiums, pp. 943–944, no translation.
Leebigs Ann. Chem. (month unavailable) 1936, 522, pp. 75–96, Osmiumsäure–ester als Zwischenprodukte bei Oxydationen; von Rudolf Criegee, no translation.

(List continued on next page.)

*Primary Examiner*—Rita Desai
*Assistant Examiner*—Hector M. Reyes
(74) *Attorney, Agent, or Firm*—Diderico van Eyl; Godfried R. Akorli

(57) ABSTRACT

This invention relates to process for dihydroxylation of olefins using transition metal catalysts to obtain monofunctional, bifunctional, and/or polyfunctional 1,2-diols of the formula (I)

$$R^1R^2C(OH)-C(OH)R^3R^4 \qquad (I)$$

where $R^1$ to $R^4$ are defined herein, by reacting an olefin of the formula (II)

$$R^1R^2C=CR^3R^4 \qquad (II)$$

where $R^1$ to $R^4$ are defined as for formula (I), with molecular oxygen in the presence of an osmium, ruthenium, or manganese compound in water or a water-containing solvent mixture at a pH of from 7.5 to 13.

14 Claims, No Drawings

OTHER PUBLICATIONS

Angewandte Chemie, 50. Jahrgang, Nr. 8, Seiten pp. 153–155, 20. Feb. 1937, Die Oxydative Spaltung der C–C–Bindung, von Dr. habil. Rudolf Criegee, no translation.

Chem. Ber. (month unavailable) 1912, pp. 3329–3337, Mitteilungen, K. A. Hofmann: Sauerstoff–Ubertragung durch Osmiumtetroxyd und Aktivierung von Chlorat_losungen, no translation.

J. AM. Chem. Soc. vol. 81, (month unavailable) 1959, pp. 4730–4733, A Study of the Hydroxylation of Olefins and the Reaction of Osmium Tetroxide with 1,2–Glycols, Nicholas A. Milas, Joseph H. Trepagnier, John T. Nolan, Jr., and Miltiadis I. Iliopulos.

J. AM. Chem. Soc. Mar. 1976–98, pp. 1986–1987, Osmium Catalyzed Vicinal Hydroxylation of Olefins by tert–Butyl Hydroperoxide under Alkaline Conditions, K. Barry Sharpless, Kageyasu Akashi.

J. Org. Chem. (month unavailable) 1981, 46, pp. 3936–3938, A greatly Improved Procedure for Ruthenium Textraoxide Catalyzed Oxidations of Organic Compounds, Per H. J. Carlsen, Tsutomu Katsuki Victor S. Martin, K. Barry Sharpless.

J. Org. Chem. (month unavailable) 1987, 52, pp. 689–691, Synthesis to Diacids and Keto Acids by Ruthenium Tetraoxide Catalyzed Oxidation of Cyclic Allylic Alcohols and α,β–Unsaturated Ketones, Francis X. Webster, Jose Rivas–Enterrios, and Robert M. Silverstein.

Tetrahedron Letters, vol. 29, No. 22. pp. 2701–2702, (month unavailable) 1988. Easy and General Method to Synthesize Chiral 2–Hydroxyacid Benzoates, V.S. Martin, M.T. Nunez and C.E. Tonn.

J. Org. Chem. (month unavailable) 1988, 53, pp. 5185–5187, Regioselective Azide Opening of 2,3–Epoxy Alcohols by [Ti(O–I–Pr)$_2$(N$_3$)$_2$]: Synthesis of α–Amino Acids, Maurice Caron, Paul R. Carlier, K. Barry Sharpless.

Tetrahedron Letters No. 23, pp 1973–1976, (month unavailable) 1976, An improved Catalytic OsO$_4$ Oxidation of Olefins to CIS–1,2–Glycols Using Tertiary Amine Oxides as the Oxidant, V. VanRheenen, R. C. Kelly and D. Y. Cha.

Tetrahedron Letters vol. 54, pp 449–450 (month unavailable) 1980, Osmium Tetroxide Catalyzed Hydroxylation of Hindered Olefins, Rahul Ray and Donald S. Matteson.

J. Org. Chem. (month unavailable) 1990, 55, pp. 766–768, Osmium Tetraoxide Catalyzed Vicinal Hydroxylation of Higher Olefins by Using Hexacyanoferrate (III) Ion as a Cooxidant, Makoto Minato, Keiji Yamamoto, and Jiro Tsuji.

Indian Journal of Chemistry, vol. 13, Feb. 1975, pp 112–115, Kinetics & Mechanism of Osmium Tetroxide Catalysed Oxidation of Maleate & Fumarate Ions with Alkaline Ferricyanide, M. P. Singh, H. S. Singh, B. S. Arya, A. K. Singh & A. K. Sisodia.

Tetrahedron Letters, vol. 32, No. 32, pp. 3965–3968, (month unavailable) 1991, On the Timing of Hydrolysis / Reoxidation in the Osmium–catalyzed Asymmertric Dihydroxylation of Olefins Using Potassium Ferricyanide as The Reoxidant, Yasukazu Ogino, Hou Chen, Hoi–Lun Kwong, and K. Barry Sharpless.

Chem. Eng. News, (month unavailable) 1994, 72(24) p. 41, Science/Technology Concentrates.

J. Chem. Soc. (C), (month unavailable) 1968, pp. 640–641, Osmium Tetroxide–catalysed Oxidation of Olefins, J.F. Cairns and H.L. Roberts.

*T. Barow, et al.: "Arylation of guanosine with para–substituted styrene oxides" Chemical Research in Toxicology, Bd. 11, Nr. 1, Januar 1998, Seiten 44–53, XP000929704 American Chemical Society, Washington, DC. US11 Seite 45, linke Spalte.

* cited by examiner

METHOD FOR THE DIHYDROXYLATION OF OLEFINS USING TRANSITION METAL CATALYSTS

The present invention relates to a process for preparing 1,2-diols from olefins using catalysts based on transition metal compounds.

1,2-Diols, in particular cis-1,2-diols, are of industrial importance as fine chemicals, solvents, starting materials for polyesters and other polymers, and also as intermediates for agrochemicals. Propylene glycol and ethylene glycol in particular are of extraordinary importance as bulk chemicals. Numerous 1,2-diols are also of commercial interest for the preparation of pharmaceuticals, cosmetics, cleaners and are employed in the textiles and plastics industries. In many cases, the carboxylic esters display a constant viscosity over, a wide temperature range, combined with a high boiling point. They are good synthetic lubricants and plasticizers.

A frequently employed method of synthesizing 1,2-diols in the university sector are "dihydroxylation reactions" such as the Sharpless dihydroxylation reaction in which olefins are reacted in the presence of osmium tetroxide and an oxidant. Review articles which describe this methodology may be found, for example, in "Asymmetric Dihydroxylation Reactions" M. Beller, K. B. Sharpless, in B. Comils, W. A. Herrmann (Eds.), VCH, 1996, Weinheim, and H. C. Kolb, M. S. Van Nieuwenhze, K. B. Sharpless, Chem. Rev. 1994, 94, 2483.

From an industrial point of view, olefins are available in virtually unlimited quantities as a source for the synthesis of diols, so that metal-catalyzed dihydroxylation reactions could in principle be used for the preparation of commercially interesting products such as propylene glycol and also fine chemicals such as 1,2-pentanediol and pinacol. Although catalytic oxidation processes are frequently superior in ecological terms to stoichiometric oxidation processes, the abovementioned products are at present produced predominantly via noncatalytic multistate processes. e.g. stoichiometric reactions with peracids or hydrogen peroxide and subsequent hydrolysis of the epoxide formed as an intermediate. This is due to the known reoxidants for manganese, ruthenium and osmium oxides being too expensive for an industrial preparation of fine and bulk chemicals and only allowing the economical preparation of extremely high-priced pharmaceutical intermediates.

The dialcohols can be synthesized stoichiometrically from olefins by reaction with $KMnO_4$ (A. J. Fatiadi, Syntiesis 1984, 85–127; W. P. Weber, J. P. Shepard, Tetrahedron Lett. 1972; 48, 4907–4908; E. Salamci, H. Segan, Y. S übeyaz, M. Balci; J. Org. Chem. 1997, 62, 2453–2557; B. G. Hazra, T. P. Kumar, P. L. Joshi, Liebigs Ann. Chem. 1997, 1029–1034). $RuO_4$ gives dialcohols by stoichiometric reaction of olefins (L. Albarella, V. Piccialli, D. Smaldone, D. Sica, J. Chem. Res. 1996, 9, 400–401) and by means of catalytic reaction using $NaIO_4$ as reoxidant (T. K. M. Shing, E. K. W. Tam, V. W. F. Tai, I. H. F. Chung, Q. Jiang, Chem. Eur. J. 1996, 2, 50–57; T. Sugai, H. Okazaki, A. Kuboki, H. Ohta, Bull. chem. Soc. Jpn. 1997, 70, 2535–2540; J. Angermann, K. Homann, H. U. Reissig, R. Zimmer Synlett 1995, 1014–1016; M. Desjardins, L. Brammer Jr., T. Hudlicky, Carbohydrate Res. 1997, 504, 39–42; M. J. Mulvihill, M. J. Miller, Tetrahedron 1998, 54, 6625–6626). Initial work on dihydroxylation by means of osmium oxide involved stoichiometric reactions (O. Makowka, Chem. Ber. 1908, 45, 943; R. Criegee, Liebigs Ann. Chem. 1936, 522, 75; R. Criegee, Angew. Chem. 1937, 50, 153). Reactions using catalytic amounts of osmium tetroxide and chlorates as reoxidants (K. A. Hoffmann, Chem. 1912, 45, 3329) or $H_2O_2$ in tert-butanol (N. A. Milas, J. H. Trepagnier, J. T. Nolan, M. Ji. Iliopolus, J. Am. Chem. Soc. 1959, 81, 4730) as reoxidant lead to overoxidation of the diols formed. Use of $H_2O_2$ results in formation of peroxoosmic acid $H_2O_2O_6$ which cleaves the diol formed as an intermediate and leads to carbonyl compounds. To reduce the overoxidation, tert-butyl hydroperoxide in the presence of $Et_4NOH$ (K. B. Sharpless, K. Akashi, J. Am. Chem. Soc. 1976, 98, 1986; P. H. J. Carlsen, T. Katsuki, V. S. Martin, K. B. Sharpless, J. Org. Chem. 1981, 46, 3936; F. X. Webster, J. Rivas-Enterrios, R. M. Silverstein, J. Org. Chem. 1987, 52, 689; V. S. Martin, M. T. Nunez, C. E. Tonn, Tetrahedron Lett. 1988, 29, 2701; M. Caron, P. R. Carlier, K. B. Sharpless. J. Org. Chem. 1988. 53. 5185). tertiary amine oxides and in most cases N-methylmorpholine N-oxide (NMO: Upjohn Process) (W. P. Schneider. A. V. McIntosh, U.S. Pat. No. 2,769,824 (1956); V. Van Rheenen, R. C. Kelly, D. Y. Cha, Tetrahedron Lett. 1976, 17, 1973) are used as reoxidants. Trimethylamine oxide is superior to NMO for trisubstituted and sometimes also tetrasubstituted alkenes (R. Ray, D. S. Matteson, Tetrahedron Lett. 1980, 21, 449). Despite the selective and catalytic dihydroxylation which is possible using N-oxides, the price of these reoxidants is prohibitive for relatively large-scale industrial applications.

In recent years, $Na_3[Fe(CN)_6]$ in the presence of sodium carbonate in a 2-phase system has been used very successfully as reoxidant for $OsO_4$ (M. Minato, K. Yamamoto, J. Tsuji, J. Org. Chem. 1990, 55, 766; M. P. Singh, H. S. Singh, B. S. Arya, A. K. Singh, A. K. Sisodia, Indian J. Chem. 1975, 13, 112), particularly also in enantioselective dihydroxylation (Y. Ogino, H. Chem, H. L. Kwong, K. B. Sharpless, Tetrahedron Lett. 1991, 32, 3965). Significant disadvantages for the synthesis of the diols on a relatively large scale are again the price and the superstoichiometric amount of iron complex to be used (3 mol=990 g per 1 mol of substrate) with addition of potassium carbonate (3 mol= 420 g). In the case of processes for the electrochemical oxidation of the $Na_4[Fe(CN)_6]$ formed in the reaction to give $Na_3[Fe(CN)_6]$ (Sepracor Inc. (Y. Gao, C. M. Zepp), PCT Int. Appl. WO 9 317 150, 1994; Anon., Chem. Eng. News. 1994, 72 (24), 41), too, industrial implementation is difficult since electrochemical processes are generally too expensive because of the apparatus required.

To circumvent the disadvantages of the abovementioned reoxidants, attempts have been made in the past to use air or oxygen for the reoxidation of $Os^{VI}$ to $Os^{VIII}$. Such a process is the most attractive method from economic and ecological points of view. However, Cairns et al. have shown that no 1,2-dialcohol is observed in the reaction of allyl alcohol, ethylene, cyclohexene and styrene in the presence of $OsO_4$ and oxygen, but in all cases overoxidation results in formation of industrially unusable amounts of the corresponding carboxylic acids, e.g. benzoic acid (styrene as substrate) and $CO_2$ (J. F. Cairns. H. L. Roberts. J Chem. Soc. (C) 1968. 6–401. In a process of Celanese Corporation (GB-B 1.028.940). too, only formic acid and heptanoic acid are obtained from 1-octene. Even in the reaction of the less oxidation-sensitive ethylene, the 1,2-diol is obtained only in traces (2% of glycol after 4 hours at an $O_2$-pressure of 7 MPa). Employees of Exxon utilize bimetallic systems comprising $OsO_4$ and Cu(II) salts (U.S. Pat. No. 4,496,779, EP-B 0 077 201, R. G. Austin, R. C. Michaelson, R. S. Myers in Catalysis in Organic Ractions (Ed: R. L. Augustine), Marcel Dekker, New York 1985, p. 269). In a manner analogous to the Wacker process, $Os^{VI}$ is reoxidized by the Cu salt which is then oxidized again by means of $O_2$.

In this process, maximum conversions of propylene are 3–5% after a reaction time of 2 hours and a pressure of 28 bar.

In summary, it can be seen that the known methods for reoxidizing osmium, ruthenium and manganese by means of molecular oxygen are not usable in dihydroxylation reactions for synthesizing dialcohols.

To avoid the abovementioned disadvantages of the known catalytic processes, it is an object of the invention to develop a novel process for metal-catalyzed dihydroxylation which is simple to carry out and gives 1,2-diols in high yield and purity, with molecular oxygen being used as reoxidant, and is suitable for industrial implementation.

This object is achieved by a process for the dihydroxylation of olefins by means of transition metal catalysts in which, according to the invention, monofunctional, bifunctional and polyfunctional 1,2-diols of the formula I,

$$R^1R^2C(OH)\text{—}C(OH)R^3R^4 \tag{I}$$

where $R^1$ to $R^4$ are each, independently of one another, hydrogen, alkyl, CN, COOH, COO-alkyl, COO-aryl, CO-alkyl, CO-aryl, O-alkyl, O-aryl, O-CO-aryl, O-CO-alkyl, OCOO-alkyl, N-alkyl$_2$, NH-alkyl, N-aryl$_2$, NH-aryl, NO, NO$_2$, NOH, aryl, fluorine, chlorine, bromine, iodine, NO$_2$, Si-alkyl$_3$, CHO, SO$_3$H, SO$_3$-alkyl, SO$_2$-alkyl, SO-alkyl, CF$_3$, NHCO-alkyl, CONH$_2$, CONH-alkyl, NHCOH, NHCOO-alkyl, CHCHCO$_2$-alkyl, CHCHCO$_2$H, PO-(aryl)$_2$, PO-(alkyl)$_2$, PO$_3$H$_2$, PO(O-alkyl)$_2$, where alkyl represents an aliphatic organic group having from 1 to 18 carbon atoms which may be linear, branched and/or cyclic and aryl is a 5-, 6- or 7-membered aromatic ring which contains from 4 to 14 carbon atoms and may be fused and contain from 0 to 3 heteroatoms such as N, O, S and where the alkyl and/or the aryl group may bear up to six further substituents selected independently from among hydrogen, alkyl, O-alkyl, OCO-alkyl, O-aryl, aryl, fluorine, chlorine, bromine, iodine, OH, NO$_2$, NO, Si-alkyl$_3$, CN, COOH, CHO, SO$_3$H, NH$_2$, NH-alkyl, N-alkyl$_2$, PO-alkyl$_2$, SO$_2$-alkyl, SO-alkyl, CF$_3$, NHCO-alkyl, COO-alkyl, CONH$_2$, CO-alkyl, NHCOH, NHCOO-alkyl, CO-aryl, COO-aryl, PO-aryl$_2$, PO$_3$H$_2$, PO(O-alkyl)$_2$, SO$_3$-alkyl, where alkyl and aryl are as defined above, are obtained by reacting olefins of the formula II

$$R^1R^2C\text{=}CR^3R^4 \tag{II}$$

where $R^1$ to $R^4$ are as defined above, with molecular oxygen in the presence of an osmium, ruthenium or manganese compound or a mixture thereof in water or a water-containing solvent mixture at a pH of from 7.5 to 13.

In particular, compounds of the formula I are prepared using olefins of the formula II in which the substituents $R^1$ to $R^4$ are each, independently of one another, hydrogen, alkyl, CN, COOH, COO-alkyl, COO-aryl, CO-alkyl, CO-aryl, O-alkyl, O-aryl, N-alkyl$_2$, aryl, fluorine, chlorine, bromine, iodine, CHO, CF$_3$, NHCO-alkyl, CONH$_2$, CONH-alkyl, NHCOO-alkyl. Here, alkyl and aryl are as defined above.

Particular preference is given to a process in which diols of the formula I in which $R^1$ to $R^4$ are each, independently of one another, hydrogen, alkyl, CN, COOH, COO-alkyl, CO-alkyl, CO-aryl, O-alkyl, O-aryl, aryl, fluorine, chlorine, bromine, CHO, NHCO-alkyl, are prepared. Here, alkyl and aryl are as defined above.

The process of the invention is carried out in the presence of water. It has been found to be advantageous to add a further organic solvent in addition to the olefin, The process of the invention can, in the case of various olefins, also be carried out in an olefin-water mixture without further solvent. Further solvents used are generally inert organic solvents. Suitable solvents are aliphatic ethers, aromatic or aliphatic hydrocarbons, alcohols and esters, halogenated hydrocarbons, dipolar aprotic solvents such as dialkyl sulfoxides, N,N-dialkylamides of aliphatic carboxylic acids and also mixtures thereof. Preference is given to alcohols, esters and ethers. As aqueous phase, use is generally made of a basic aqueous solution having a pH of from 7.5 to 13. The basic pH of the solution is achieved by addition of a base to the water. It is generally advantageous to carry out the reaction in buffered aqueous solutions, preferably having a pH of from 8 to 13. The buffered solution is prepared by addition of known buffers to water.

To enable the diol products to be separated off readily, it is sometimes advantageous to use an aqueous salt solution or a buffered aqueous salt solution, for example an aqueous solution of an alkali metal halide or alkaline earth metal halide, as solvent in place of water or buffered aqueous solutions.

In the process of the invention, molecular oxygen or a gas mixture comprising molecular oxygen is used as oxidant. Preference is given to gas mixtures comprising at least 15% by volume of oxygen. Particular preference is given to air and oxygen gas having an oxygen content of <95%.

The reaction preferably proceeds at temperatures of from 20 to 200° C. in many cases, it has been found to be useful to employ temperatures of from 30 to 150° C. preferably from 40 to 100° C. The process of the invention can be carried out under atmospheric pressure, e.g. by passing oxygen through the reaction solution. However, the reaction rate is increased when a superatmospheric oxygen pressure is employed. The process can be carried out at pressures of up to 200 bar, but is usually carried out at a pressure of up to 60 bar and preferably in the range from atmospheric pressure to 20 bar.

To achieve selectivity of the dihydroxylation reaction, the catalyst is activated by addition of an amine. Amines suitable for this purpose are, in particular, tertiary amines such as trialkylamines, dialkylarylamines, alkyldiarylamines, which may be cyclic and/or linear, pyridines and quinolones. Preference is given to bicyclic amines such as 1,4-diazabicyclo[2,2,2]octane and also compounds of the quinuclidine type and substituted phthalazines, diphenylpyrimidines and carbamoylindolines.

The transition metal catalysts used are generally oxides of the elements osmium, manganese and ruthenium, preferably osmium. These metals are generally used in oxidation states of >+4. However, it is also possible to use catalyst precursors in lower oxidation states. Thee are converted under the reaction conditions into the catalytically active Os(VIII) and Os(VI) species or Mn(VII) or Ru(VIII) species. Examples of osmium catalysts or catalyst precursors which can be used are: OsO$_4$, K$_2$Os$_2$(OH)$_4$, Na$_2$Os$_2$(OH)$_4$, OS$_3$(CO)$_{12}$, OsCl$_3$, H$_2$OsCl$_6$, [CF$_3$SO$_3$Os(NH$_3$)$_5$](O$_3$SCF$_3$)$_2$, OsO$_4$ on vinylpyridine, Bu$^t$NOsO$_3$. Examples manganese catalysts or catalyst precursors which can be used are: MnO$_2$, KMnO$_4$, Ca(MnO$_4$)$_2$, MnCl$_3$, Mn(OAc)$_3$. Examples of ruthenium catalysts or catalyst precursors which can be used are: RuCl$_3$, RuO$_4$, RuO$_2$.

In the process of the invention, the catalyst is used in catalytic amounts relative to the olefin. In general, use is made of from 0.2 to 0.00001 equivalents, based on olefin, preferably from 0.1 to 0.0001 equivalents and particularly preferably from 0.1 to 0.0005 equivalents. The ratio of amine to metal is from 0.01:1 to 1.000:1 preferably from 0.1:1 to 100:1. Particular preference is given to using ratios of amine to osmium of from 1:1 to 50:1.

When using bulky olefins, in particular trisubstituted and tetrasubstituted olefins, it is sometimes advantageous to add a cocatalyst to hydrolyze the metal ester formed as an intermediate. This cocatalyst is an amide which aids hydrolysis, for example a sulfonamide or/and carboxamide. Particular preference is given to the addition of methylsulfonamide.

The cocatalyst is used in an amount of from 0.01 mol% to 10 mol% (based on olefin), preferably from 0.1 to 5 mol%.

The particular advantage of the process of the invention is the use of oxygen or oxygen-containing gases as reoxidant. Despite the comparatively difficult reoxidation process, high catalyst productivities can be achieved by mixing the aqueous catalyst phase which has been used once with olefin again. In this way, the catalyst costs for the process of the invention are minimized, so that even industrial processes can be carried out economically.

The process of the invention is particularly surprising and novel since no catalyzed, selective dihydroxylation reactions to form 1,2-diols using oxygen as reoxidant have been described in the past. This is attributable to the few previous studies using oxygen as reoxidant leading essentially to overoxidation, if any reaction at all occurred. The novel combination described in the process of the invention of addition of a ligand which accelerates the dihdyroxylation and carrying out the process in a buffered basic solution surprisingly leads to a chemoselective dihydroxylation process even in the presence of oxygen. The process of the invention shows for the first time that the statements in the known literature on the catalyzed dihydroxylation using oxygen are wrong.

The particular advantages of the novel process are the price advantage of the oxidant, the simple way in which the process can be carried out and the high selectivity of the process compared with other oxidants which have been employed.

The 1,2-diols prepared according to the invention can be used, inter alia, as solvents, starting materials for polyesters and other polymers, intermediates for agrochemicals, cosmetics, cleaners and are employed in the form of their esters as synthetic lubricants and plasticizers.

The following examples illustrate the process of the invention without restricting it to the specific examples presented.

EXAMPLES

Example 1

18.4 mg of $K_2OsO_4 \times 2H_2O$ (0.05 mmol) are weighed into a Schlenk vessel. While stirring by means of a magnetic stirrer, 25 ml of 0.4–0.5 molar $Na_3PO_4/Na_2HPO_4$ buffer solution having a pH of 11.2 and 10 ml of 2-methyl-2-propanol are added, resulting in formation of 2 phases. The vessel is heated to 50° C. on a water bath and flushed with oxygen. After addition of 173 μl of styrene (1.5 mmol), the reaction vessel is connected to a burette filled with oxygen, and the reaction solution is stirred at 50° C. under a slightly superatmospheric $O_2$ pressure (about 50 cm of water) for 24 hours.

The reaction mixture is worked up as described below:

2 g of sodium bisulfite and 10 ml of ethyl acetate are added to the reaction solution. After stirring for 10 minutes, the upper organic phase is separated off and the aqueous phase is shaken with 10 ml of ethyl acetate. The organic phases are purified, dried over anhydrous sodium sulfate and evaporated to dryness on a rotary evaporator.

This gives 130 mg of (R)/(S)-1-phenyl-1,2-ethanediol, 63% (based on styrene). To isolate any acidic products formed, the aqueous solution is acidified and shaken twice with 15 ml each time of ether. This gives 20 mg of a crystalline product, of which more than 90% is made up by benzoic acid.

Example 2

18.4 mg of $K_2OsO_4 \times 2H_2O$ (0.05 mmol) are weighed into a Schlenk vessel. While stirring by means of a magnetic stirrer, 25 ml of 0.3 molar borax NaOH buffer solution having a pH of 10.2. 4 g of NaCl and 10 ml of 2-meth-2-propanol are added 2 phases are formed. The vessel is heated to 50° C. on a water bath and flushed with oxygen. After addition of 288 μl of styrene (2.5 mmol), the reaction vessel is connected to a burette filled with oxygen, and the reaction solution is stirred at 50° C. under a slightly superatmospheric $O_2$ pressure (50 cm of water) for 24 hours. The reaction mixture is worked up as described in example 1.

This gives 215 mg of (R)/(S)-1-phenyl-1,2-ethanediol (62%) and 101 mg of benzoic acid.

Example 3

1.5 mmol of styrene are reacted as described in example 1, but the reaction temperature was 30° C. and the reaction time was 62 hours. After work-up, this gives 104 mg of (R)/(S)-1-phenyl-1,2-ethanediol (50%) and 15 mg of benzoic acid.

Example 4

The procedure of example 1 is repealed, but 0.05 mmol of 1,4-diazabicyclo[2.2.2]octane are added to the osmium salt. This gives 151 mg of (R)/(S)-1-phenyl-1,2-ethanediol (72%) and 31 mg of benzoic acid.

Example 5

The procedure of example 1 is repeated using 231 mg of 2-vinylnaphthalene (1.5 mmol) as substrate. As a difference from example 1, the reaction time was 7 hours. After work-up, this gives 214 mg of (R)/(S)-1-(2-naphthyl)-1,2-ethanediol (76%). 34 mg of a crystalline product consisting predominantly of 2-naphthalene-carboxylic acid are obtained from the ether solution.

Example 6

Using a method analogous to example 1, 18.4 mg of $K_2OsO_4 \times 2H_2O$ (0.05 mmol) are reacted with 130 μl (1 mmol) of α-methylstyrene in the 2-phase system described.

After work-up in the manner indicated, this gives 110 mg of (R)/(S)-2-phenyl-1,2propanediol (72%).

Example 7

Using a method analogous to example 1, 18.4 mg of $K_2OsO_4 \times 2H_2O$ (0.05 mmol) are reacted with 130 μl (1 mmol) of trans-β-methylstyrene.

After the usual work-up, this gives 108 mg of 1-phenyl-1,2-propanediol (71%).

Example 8

Using a method analogous to example 1, 18.4 mg of $K_2OsO_4 \times 2H_2O$ (0.05 mmol) are reacted with 203 μl (2 mmol) of cyclohexene.

After the usual work-up, this gives 196 mg of cis-cyclohexanediol (84%).

Example 9

7.4 mg of $K_2OsO_4 \times 2H_2O$ (0.02 mmol) are weighed into a Schlenk vessel. While stirring by means of a magnetic stirrer, 25 ml of a buffer solution having a pH of 10.4 and prepared from 0.5 molar $K_2HPO_4$ solution and 2 molar NaOH, together with 10 ml of 2-methyl-2-propanol are added, resulting in formation of 2 phases. The vessel is heated to 50° C. on a water bath and flushed with oxygen. After addition of 230 µl of styrene (2 mmol), the reaction vessel is connected to a burette filled with oxygen, and the reaction solution is stirred at 50° C. under a slightly super-atmospheric $O_2$ pressure (about 50 cm of water) for 24 hours.

The reaction mixture was worked up as described below:

2 g of sodium bisulfite and 20 ml of ethyl acetate are added to the reaction solution. After stirring for 10 minutes, the upper organic phase is separated off. Dialcohol and unreacted olefin are determined by means of GC.

Yield of 1-phenyl-1,2-ethanediol: 43% (selectivity: 57%).

Example 10

The procedure of example 9 is repeated, but 0.06 mmol of 1,4-diazabicyclo[2,2,2]octane are added to the osmium salt.

Yield of 1-phenyl-1,2-ethanediol: 43% (selectivity: 78%).

Example 11

The procedure of example 10 is repeated using 308 mg of 2-vinylnaphthalene (2 mmol) as substrate. Dialcohols and unreacted olefin are determined by means of HPLC in this case.

Yield of 1-(2-naphthyl)-1,2-ethanediol: 56% (selectivity: 75%).

Example 12

7.4 mg of $K_2OsO_4 \times 2H_2O$ (0.02 mmol)/0.02 mmol of DABCO are reacted with 318 µl of 1-phenyl-1-cyclohexene (2 mmol) using the procedure described in example 9, but using a buffer solution having a ph of 11.2.

Yield of 1-phenyl-1,2-cyclohexanediol: 81% (selectivity 84%)

Example 13

3.7 mg of $K_2OsO_4 \times 2H_2O$ (0.01 mmol) are reacted with 260 µl of α-methylstyrene (2 mmol) using the procedure described in example 9 but for a reaction time of 12 hours.

Yield of 2-phenyl-1,2-propanediol: 92% (selectivity: 92%).

Example 14

The procedure of example 13 is repeated, but 0.03 mmol of 1,4-diazabicyclo[2.2.2]octane are added to the osmium salt. Reaction time=16 h.

Yield of 2-phenyl-1,2-propanediol: 98% (selectivity: 98%).

Example 15

Cyclohexane is reacted using a procedure analogous to example 14. Reaction time=24 h.

Yield of 1,2-cyclohexanediol: 68% (selectivity: 75%).

Example 16

1-Octene is reacted using a procedure analogous to example 14. Reaction time=15 h.

Yield of 1,2-octanediol: 96% (selectivity: 97%).

Example 17

1.9 mg of $K_2OsO_4 \times 2H_2O$ (0.05 mmol) are reacted with 260 µl of α-methylstyrene (2 mmol) with addition of 0.015 mmol of 1,4-diazabicyclo[2.2.2]octane using the procedure described in example 9.

Yield of 2-phenyl-1,2-propanediol: 96% (selectivity 96%).

Example 18

7.4 mg of $K_2OsO_4 \times 2H_2O$ (0.02 mmol)/0.06 mmol of DABCO are reacted with 240 µl of 1-methyl-1-cyclohexene (2 mmol) using the procedure described in example 9, but for a reaction time of 14 h and using a buffer solution having a pH of 11.2.

Yield of 1-methyl-1,2-cyclohexanediol: 78% (selectivity: 80%).

Example 19

320 µl of allyltrimethylsilane (2 mmol) are reacted using a procedure analogous to example 18 but at a pH of 10.4.

Yield of 3-(trimethylsilyl)-1,2-propanediol: 72% (selectivity: 83%).

Example 20

14.7 mg of $K_2OsO_4 \times 2H_2O$ (0.04 mmol)/0.12 mmol of DABCO are reacted with 380 µl (2 mmol) of trans-5-decene using the procedure described in example 9, but for a reaction time of 18 h and using a buffer solution having a pH of 12.0.

Yield of 5,6-decanediol: 85% (selectivity: 96%).

Example 21

240 µl of 2,3-dimethyl-2-butene (2 mmol) are reacted using a method analogous to example 20.

Yield of 2,3-dimethyl-2,3-butanediol: 99% (selectivity: 99%).

Example 22

245 µl of 2-methyl-2-pentene (2 mmol) are reacted at pH=11.2 using a method analogous to example 20.

Yield of 2-methyl-2,3-pentanediol: 88% (selectivity: 87%).

Example 23

692 mg of 1H,1H,2H-perfluoro-1-octene (2 mmol) are reacted at pH=10.4 using a method analogous to example 20.

Yield of 1H,1H,2H-perfluorooctane-1,2-diol: 53% (selectivity: 84%).

Example 24

245 µl of 2-vinyl-1,3-dioxolane (2 mmol) are reacted using a procedure analogous to example 23.

Yield of 2-(1,2-dihydroxyethyl)-1,3-dioxolane: 59% (selectivity: 97%).

Example 25

7.4 mg of $K_2OsO_4 \times 2H_2O$ (0.02 mmol)/0.06 mmol of DABCO are reacted with 275 µl of allyl phenyl ether (2 mmol) using the procedure described in example 9. Reaction time=18 h.

Yield of 3-phenoxy-1,2-propanediol: 50% (selectivity: 96%).

Example 26

295 μl of allyl phenyl sulfide (2 mmol) are reacted using a method analogous to example 25.

Yield of 2,3-dihydroxypropyl phenyl sulfide: 51% (selectivity: 94%)

Example 27

0.002 mmol of $K_2OsO_4 \times 2H_2O$ dissolved in water. 0.006 mmol of DABCO and 25 ml of a buffer solution having a ph of 10.4 and prepared from 0.5 molar $K_2HPO_4$ solution and 2 molar NaOH, together with 12 ml of 2-methyl-2-propanol are placed in a glass vessel located in an autoclave. The mixture is stirred by means of a magnetic stirrer and two phases are formed. After addition of 260 μl of α-methylstyrene (2 mmol), the autoclave is pressurized with 5 bar of oxygen and is heated to 50–55° C.

After 24 hours, the reaction mixture is worked up as described in example 9.

Yield of 2-phenyl-1,2-propanediol: 94% (selectivity: 94%).

Example 28

0.005 mmol of $K_2OsO_4 \times 2H_2O$/0.015 mmol of DABCO are reacted with 650 μl of α-methylstyrene (5 mmol) under an $O_2$ pressure of 5 bar using the procedure described in example 27.

Yield of 3-phenyl-1,2-propanediol: 95% (selectivity: 95%).

Example 29

The procedure of example 27 is repeated, but the autoclave is pressurized with 5 bar of compressed air in place of pure oxygen.

Yield of 2-phenyl-1,2-propanediol: 41% (selectivity: 93%).

Example 30

The procedure of example 29 is repeated, but the autoclave is pressurized with 10 bar of compressed air.

Yield of 2-phenyl-1,2-propanediol: 76% (selectivity: 92%).

What is claimed is:

1. A process for the dihydroxylation of olefins using transition metal catalysts to obtain monofunctional, bifunctional, and/or polyfunctional 1,2-diols of the formula (I)

$$R^1R^2C(OH)-C(OH)R^3R^4 \qquad (I)$$

where $R^1$ to $R^4$ are each, independently of one another, hydrogen, alkyl, CN, COOH, COO-alkyl, COO-aryl, CO-alkyl, CO-aryl, O-alkyl, O-aryl, O-CO-aryl, O-CO-alkyl, OCOO-alkyl, N-alkyl$_2$, NH-alkyl, N-aryl$_2$, NH-aryl, NO, NO$_2$, NOH, aryl, flourine, chlorine, bromine, iodine, Si-alkyl$_3$, CHO, SO$_3$H, SO-$_3$-alkyl, SO-$_2$-alkyl, SO-alkyl, CF$_3$, NHCO-alkyl, CONH$_2$, CONH-alkyl, NHCOH, NHCOO-alkyl, CHCHCO$_2$-alkyl, CHCHCO$_2$H, PO-(aryl)$_2$, PO(alkyl)$_2$, PO$_3$H$_2$, or PO(O-alkyl)$_2$, where alkyl is a liner, branched, or cyclic aliphatic organic group having from 1 to 18 carbon atoms and aryl is a 5-, 6-, or 7-membered aromatic ring containing from 4 to 14 carbon atoms and from 0 to 3 heteroatoms and is optionally fused, and where the alkyl or the aryl group optionally bears up to six substituents selected independently from the group consisting of hydrogen, alkyl, O-alkyl, OCO-alkyl, O-aryl, aryl, fluorine, chlorine, bromine, iodine, OH, NO$_2$, NO, Si-alkyl$_3$, CN, COOH, CHO, SO$_3$H, NH$_2$, NH-alkyl, N-alkyl$_2$, PO-alkyl$_2$, SO$_2$-alkyl, SO-alkyl, CF$_3$, NHCO-alkyl, COO-alkyl, CONH$_2$, CO-alkyl, NHCOH, NHCOO-alkyl, CO-aryl, COO-aryl, PO-aryl$_2$, PO$_3$H$_2$, PO(O-alkyl)$_2$, and SO$_3$-alkyl, where alkyl and aryl are as defined above, comprising reacting an olefin of the formula (II)

$$R^1R^2C=CR^3R^4 \qquad (II)$$

where $R^1$ to $R^4$ are defined as for formula (I), with an oxidant comprising molecular oxygen or a gas mixture comprising molecular oxygen in the presence of an osmium, ruthenium, or manganese compound in water or a water-containing solvent mixture at a pH of from 7.5 to 13; and adding an amine to achieve improved selectivity.

2. The process according to claim 1 for preparing compounds of the formula (I) wherein for olefins of the formula (II) the substituents $R^1$ to $R^4$ are each, independently of one another, hydrogen, alkyl, CN, COOH, COO-alkyl, COO-aryl, CO-alkyl, CO-aryl, O-alkyl, O-aryl, N-alkyl$_2$, aryl, fluorine, chlorine, bromine, iodine, CHO, CF$_3$, NHCO-alkyl, CONH$_2$, CONH-alkyl, or NHCOO-alkyl.

3. The process according to claim 1 wherein diols of the formula (I) in which $R^1$ to $R^4$ are each, independently of one another, hydrogen, alkyl, CN, COOH, COO-alkyl, CO-alkyl, CO-aryl, O-alkyl, O-aryl, aryl, fluorine, chlorine, bromine, CHO, or NHCO-alkyl are prepared.

4. The process according to claim 1 wherein the oxidant is a gas mixture comprising at least 15% by volume of oxygen.

5. The process according to claim 1 wherein the reaction proceeds at a temperature of from 20 to 200° C. and a pressure of up to 200 bar.

6. The process according to claim 1 wherein the amine is a tertiary amine.

7. The process according to claim 1 wherein the amine is a bicyclic amino of the quinuclidine type.

8. The process according to claim 1 wherein a sulfonamide is added as a cocatalyst.

9. The process according to claim 8 wherein the sulfonamide cocatalyst is a methylsulfonamide or a carboxamide.

10. The process according to claim 1 wherein the osmium compounds OsO$_4$, K$_2$Os$_2$(OH)$_4$, Na$_2$OS$_2$(OH)$_4$, OS$_3$(CO)$_{12}$, OsCl$_3$, H$_2$OsCl$_6$, [CF$_3$SO$_3$Os(NH$_3$)$_5$](O$_3$SCF$_3$)$_2$, OsO$_4$ on vinylpyridine, or Bu$^t$NOsO$_3$ are used as catalysts or catalyst precursors.

11. The process according to claim 1 wherein the manganese compounds MnO$_2$, KMnO$_4$, Ca(MnO$_4$)$_2$, MnCl$_3$, or Mn(OAc)$_3$ are used as catalysts or catalyst precursors.

12. The process according to claim 1 wherein the ruthenium compounds RuCl$_3$, RuO$_4$, or RuO$_2$ are used as catalysts or catalyst precursors.

13. The process according to claim 1 wherein the catalyst is used in amounts of from 0.2 to 0.0001 equivalents, based on the olefin.

14. The process according to claim 1 wherein the ratio of amine to metal is from 0.01:1 to 1 000:1.

* * * * *